US012687648B2

(12) United States Patent
Ryu

(10) Patent No.: US 12,687,648 B2
(45) Date of Patent: Jul. 21, 2026

(54) RADIOGRAPHY APPARATUS, RADIOGRAPHY SYSTEM, AND CONTROL METHOD OF RADIOGRAPHY APPARATUS

(71) Applicant: CANON KABUSHIKI KAISHA, Tokyo (JP)

(72) Inventor: Takuya Ryu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 112 days.

(21) Appl. No.: 18/761,069

(22) Filed: Jul. 1, 2024

(65) Prior Publication Data

US 2025/0012933 A1    Jan. 9, 2025

(30) Foreign Application Priority Data

Jul. 4, 2023    (JP) ................................. 2023-110077

(51) Int. Cl.
*G01T 1/24*        (2006.01)
*A61B 6/00*        (2006.01)

(52) U.S. Cl.
CPC .............. *G01T 1/243* (2013.01); *G01T 1/247* (2013.01); *A61B 6/54* (2013.01)

(58) Field of Classification Search
CPC ........... G01T 1/243; G01T 1/247; A61B 6/54; A61B 6/56
See application file for complete search history.

(56) References Cited

U.S. PATENT DOCUMENTS

2006/0054829 A1*   3/2006   Tsuchino ............. A61B 6/4488
                                                     250/370.09
2013/0129048 A1*   5/2013   Chicchetti ............ A61B 6/4452
                                                     378/62

FOREIGN PATENT DOCUMENTS

JP        2002214729 A      7/2002
JP        2005087254 A      4/2005

* cited by examiner

*Primary Examiner* — Kiho Kim

(74) *Attorney, Agent, or Firm* — Canon U.S.A., Inc. IP Division

(57)        ABSTRACT

A radiography apparatus includes a plurality of pixels configured to generate image signals that are based on radiation, a voltage conversion circuit configured to convert an input voltage and output the converted voltage, a first battery configured to output a voltage, and a power control unit configured to supply either of the voltage output by the voltage conversion circuit and the voltage output by the first battery as a source voltage, depending on an operating state of the radiography apparatus.

20 Claims, 9 Drawing Sheets

RADIOGRAPHY APPARATUS, RADIOGRAPHY SYSTEM, AND CONTROL METHOD OF RADIOGRAPHY APPARATUS

BACKGROUND

Field of the Disclosure

The present disclosure relates to a radiography apparatus, a radiography system, and a control method of a radiography apparatus.

Description of the Related Art

In recent years, as an imaging apparatus to be used for medical image diagnosis or a non-destructive inspection that uses X-rays and the like, a radiography apparatus that uses a flat panel detector (hereinafter, abbreviated as an FPD) formed of a semiconductor material has been used. This FPD includes a pixel array in which a plurality of pixels that convert radiation into electric signals is arrayed in a two-dimensional matrix, and outputs a digital radiation image corresponding to one image (frame) by converting electric signals from the pixel array into digital data. Such a radiography apparatus is used as a digital imaging apparatus for still image capturing, such as plain radiography or moving image capturing, such as fluoroscopy, in medical image diagnosis, for example. In such an imaging apparatus, for further reduction in invasiveness and further improvement in diagnosis quality, there is a demand for a sensor with higher sensitivity and a higher signal-to-noise ratio (SN ratio) that enables a sharp image to be captured even with a small radiation dose.

On the other hand, a radiography apparatus includes a switching power source, such as a direct current to direct current (DC/DC) power source, that supplies a voltage to each circuit substrate. By being switched at high frequency, the switching power source generates high-frequency radiation noise. Because a radiation sensor in a radiation image detector that includes a sensor array in which photoelectric conversion elements are two-dimensionally arranged handles small signals, the radiation sensor is susceptible to radiation noise and causes an increase in noise in captured images.

Japanese Patent Application Laid-Open No. 2002-214729 discusses employing a configuration in which a housing has a partition, and a radiation sensor and a source circuit are stored in different sections, and a method of reducing the effect of radiation noise generated from a source circuit unit on the radiation sensor.

Japanese Patent Application Laid-Open No. 2005-87254 discusses a method of reducing the influence of noise by controlling a drive cycle of a switching power source and a scan cycle of a sensor.

Nevertheless, in the method discussed in Japanese Patent Application Laid-Open No. 2002-214729, because the radiation sensor and the source circuit unit are arranged separately using the partition formed by the housing and a lid member, an issue arises in which the size on a panel horizontal surface of a radiation image detector increases.

In the method discussed in Japanese Patent Application Laid-Open No. 2005-87254, it is necessary to strictly synchronize the drive cycle of the switching power source and the scan timing of the sensor for each scanning line. In a case where the amount of noise changes, there may be a case where noise cannot be sufficiently reduced.

SUMMARY

Embodiments of the present disclosure are directed to providing a radiography apparatus that can reduce the influence of noise from a voltage conversion circuit.

According to an aspect of the present disclosure, a radiography apparatus includes a plurality of pixels configured to generate image signals that are based on radiation, a voltage conversion circuit configured to convert an input voltage and output the converted voltage, a first battery configured to output a voltage, and a power control unit configured to supply either of the voltage output by the voltage conversion circuit and the voltage output by the first battery as a source voltage, depending on an operating state of the radiography apparatus.

Further features of various embodiments will become apparent from the following description of exemplary embodiments with reference to the attached drawings.

DESCRIPTION OF THE EMBODIMENTS

Figure 1:
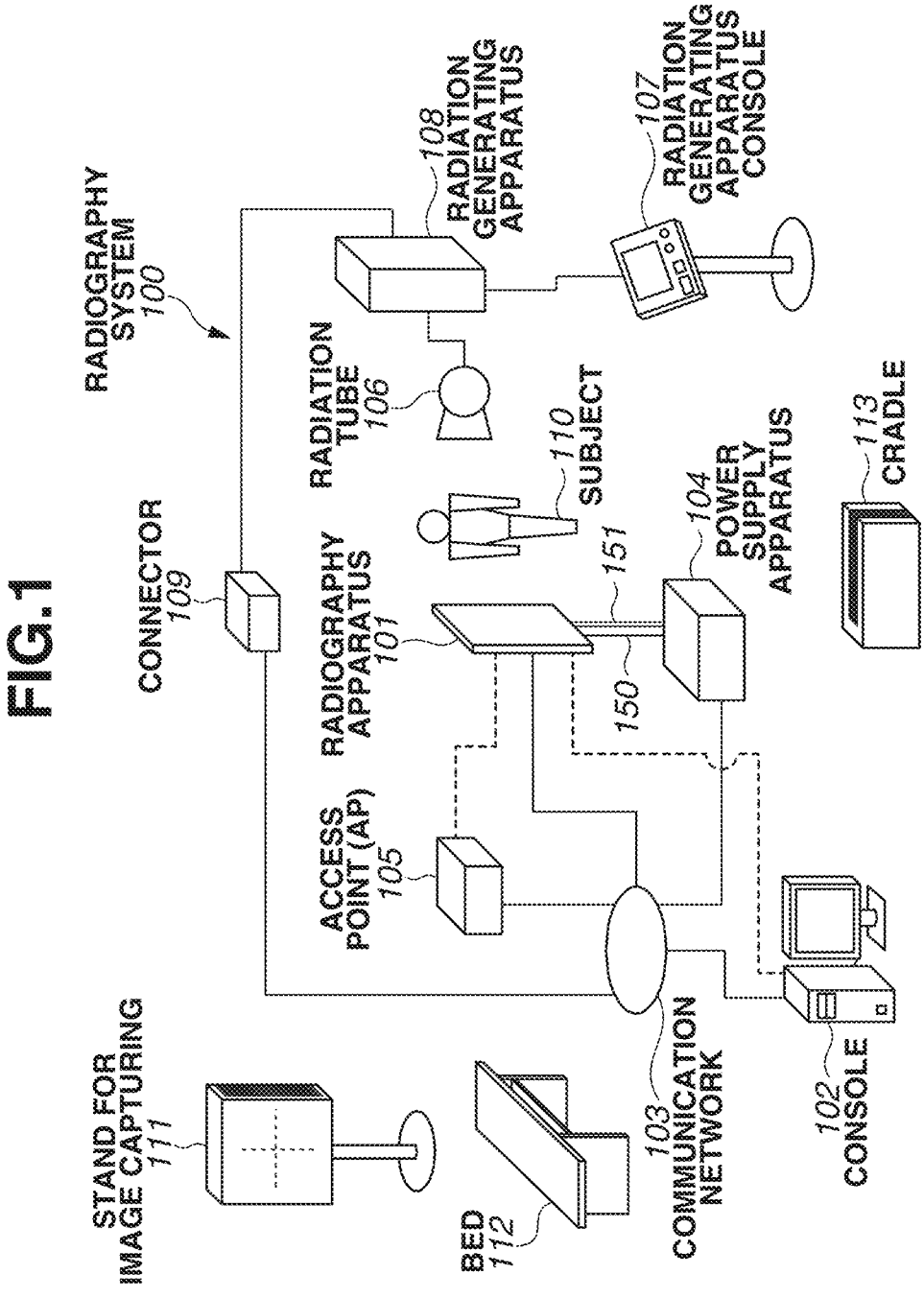
FIG. 1 is a diagram illustrating an example of a configuration of a radiography system according to a first exemplary embodiment.

Hereinafter, specific exemplary embodiments of a radiography system will be described with reference to the drawings. In the following description and the drawings, components common to a plurality of drawings are assigned the same reference numerals. Thus, the common components will be described with reference to the plurality of drawings, and the description of the components assigned the same reference numerals will be appropriately omitted. The radiation in this specification can include alpha (α) rays, beta (β) rays, and gamma (γ) rays, which are beams created by particles (including photons) released by radioactive decay, and also include beams with energy at an equal level or a higher level, such as X-rays, particle rays, and cosmic rays, for example.

FIG. 1 is a diagram illustrating an example of a configuration of a radiography system 100 according to a first exemplary embodiment. The radiography system 100 includes a radiography apparatus 101, a console 102, a communication network 103, a power supply apparatus 104, an access point (AP) 105, a radiation tube 106, and a radiation generating apparatus console 107. The radiography system 100 further includes a radiation generating apparatus 108, a connector 109, a stand for image capturing 111, a bed 112, and a cradle 113.

The radiography apparatus 101 includes a sensor unit for acquiring radiation images, has a wired or wireless communication function or both of the wired and wireless communication functions, and can transmit and receive data to and from the console 102 via a communication path.

The console 102 is constituted by a personal computer (PC) including a display function of providing display, such as a monitor, and an input function of receiving an input from a user, and can transmit an instruction from the user to the radiography apparatus 101, receive an image acquired by the radiography apparatus 101, and present the image to the user. In addition, the console 102 has a wired or wireless communication function or both of the wired and wireless communication functions. In the configuration illustrated in FIG. 1, a stationary console is illustrated as the console 102, but in the actual operation of the radiography system 100, the type of the console 102 is not specifically limited, and a portable laptop PC or a tablet device may be used as the console 102.

Depending on the configuration state of the radiography system 100, the radiography apparatus 101 may transmit image data to the console 102 via any of the communication network 103, the power supply apparatus 104, and the AP 105 that are included in the communication path. Alternatively, the radiography apparatus 101 may directly transmit image data to the console 102. The communication network 103 is a local area network (LAN), for example. By connecting the radiography apparatus 101 and the console 102 to the communication network 103 via a wired cable, transmission and reception of data to and from each other is allowed.

The radiography apparatus 101 has a function of receiving power. By connecting the power supply apparatus 104 that can supply power to the radiography apparatus 101, it becomes possible to supply power from the power supply apparatus 104 to the radiography apparatus 101. Furthermore, in a case where the radiography apparatus 101 and the power supply apparatus 104 have a communication function, a power receiving unit of the radiography apparatus 101 and a power supply unit of the power supply apparatus 104 may be provided with a configuration of performing communication. With this configuration, by connecting the radiography apparatus 101 and the power supply apparatus 104, the radiography apparatus 101 becomes able to receive power and perform communication via the power supply apparatus 104. The power receiving method and the communication method may be whichever of a method using an electric contact and a contactless method.

In the configuration illustrated in FIG. 1, among lines that connect the radiography apparatus 101 and the power supply apparatus 104, a line 150 indicates a (wired and/or wireless) connection line for communication, and a line 151 indicates a connection line for power supply. In the configuration illustrated in FIG. 1, a configuration in which the power supply apparatus 104 is connected to the console 102 via the communication network 103 is illustrated, but the configuration is not limited to this. The power supply apparatus 104 and the console 102 may be configured to be electrically connected directly.

In a case where the radiography apparatus 101 is provided with a wireless communication function, the radiography apparatus 101 may implement data transmission and reception with the console 102 via the AP 105. In the configuration illustrated in FIG. 1, a configuration in which the AP 105 is connected to the console 102 via the communication network 103, but similarly to the above-described power supply apparatus 104, the AP 105 may be electrically connected to the console 102 directly.

Furthermore, in a case where the radiography apparatus 101, the console 102, the power supply apparatus 104, and the AP 105 have a function of directly transmitting and receiving data to and from each other, data may be directly transmitted to and received from each other in a wireless or wired manner.

Heretofore, an example of a path of data transmission and reception between the radiography apparatus 101 and the console 102 has been described.

The cradle 113 serving as a charger of the radiography apparatus 101 will now be described. Although an internal configuration of the radiography apparatus 101 will be described below, the radiography apparatus 101 includes an internal power source, such as a battery, and the internal power source can be charged by supplying power to the radiography apparatus 101 from the outside and the like. The internal power source can also be charged by receiving power from the power supply apparatus 104 as described above. However, in a case where, for example, a radiation image is not to be captured, the cradle 113 may be prepared in the radiography system 100 as a device that can charge the internal power source, by assembling the radiography apparatus 101 thereto.

In the configuration illustrated in FIG. 1, an example in which the cradle 113 is independently provided without performing communication with other components of the radiography system 100 is illustrated, but the configuration is not limited to this example. A plurality of cradles 113 having a communication function may be configured to be connected with the other components of the radiography system 100 via the communication network 103. For example, while the radiography apparatus 101 is assembled to the cradle 113, communication may be made executable between the radiography apparatus 101 and another component, such as the console 102, via the cradle 113.

Next, the overview of image capturing of a subject 110 that uses radiation will be described. To capture an image of the subject 110, the radiography apparatus 101 is installed at a position where the radiography apparatus 101 can receive radiation emitted from the radiation tube 106 and having passed through the subject 110.

An example of a flow of image capturing will be described. After a user, such as an operator, activates the radiography apparatus 101, the user operates the console 102 to bring the radiography apparatus 101 into an image capturing executable state. Subsequently, the user operates the radiation generating apparatus console 107 to set image capturing conditions (tube voltage, tube current, irradiation time, etc. of the radiation tube 106) under which radiation is to be emitted. After finishing the above-described processing, the user confirms that image capturing preparation including the subject 110 has been completed, and presses an exposure switch or irradiation switch provided on the radiation generating apparatus console 107 to cause radiation to be emitted from the radiation tube 106 via the radiation generating apparatus 108. The radiation tube 106 is a radiation source that emits radiation.

When radiation is to be emitted, the radiation generating apparatus 108 notifies the radiography apparatus 101 of a signal indicating that radiation is going to be emitted, via the connector 109 and the communication network 103. In the configuration illustrated in FIG. 1, the radiography apparatus 101 and the radiation generating apparatus 108 are connected via the connector 109 and the communication network 103, but a connection configuration is not limited to this configuration. In a similar manner to the connection configuration described above, the radiography apparatus 101 and the radiation generating apparatus 108 may be directly connected.

If the radiography apparatus 101 receives the signal indicating that radiation is going to be emitted, the radiography apparatus 101 confirms whether preparation for irradiation of radiation has been completed, and if there is no problem with the preparation, the radiography apparatus 101 returns an irradiation permission to the radiation generating apparatus 108. Radiation is accordingly emitted.

If the radiography apparatus 101 detects the end of irradiation of radiation using various methods, such as a method of referring to a notification from the radiation generating apparatus 108 or a predetermined set time, the radiography apparatus 101 starts to generate image data of a radiation image. The generated image data is transmitted to the console 102 through the above-described communication path. The image data transmitted to the console 102 can be displayed as a radiation image on a display unit included in the console 102, for example.

Figure 2:
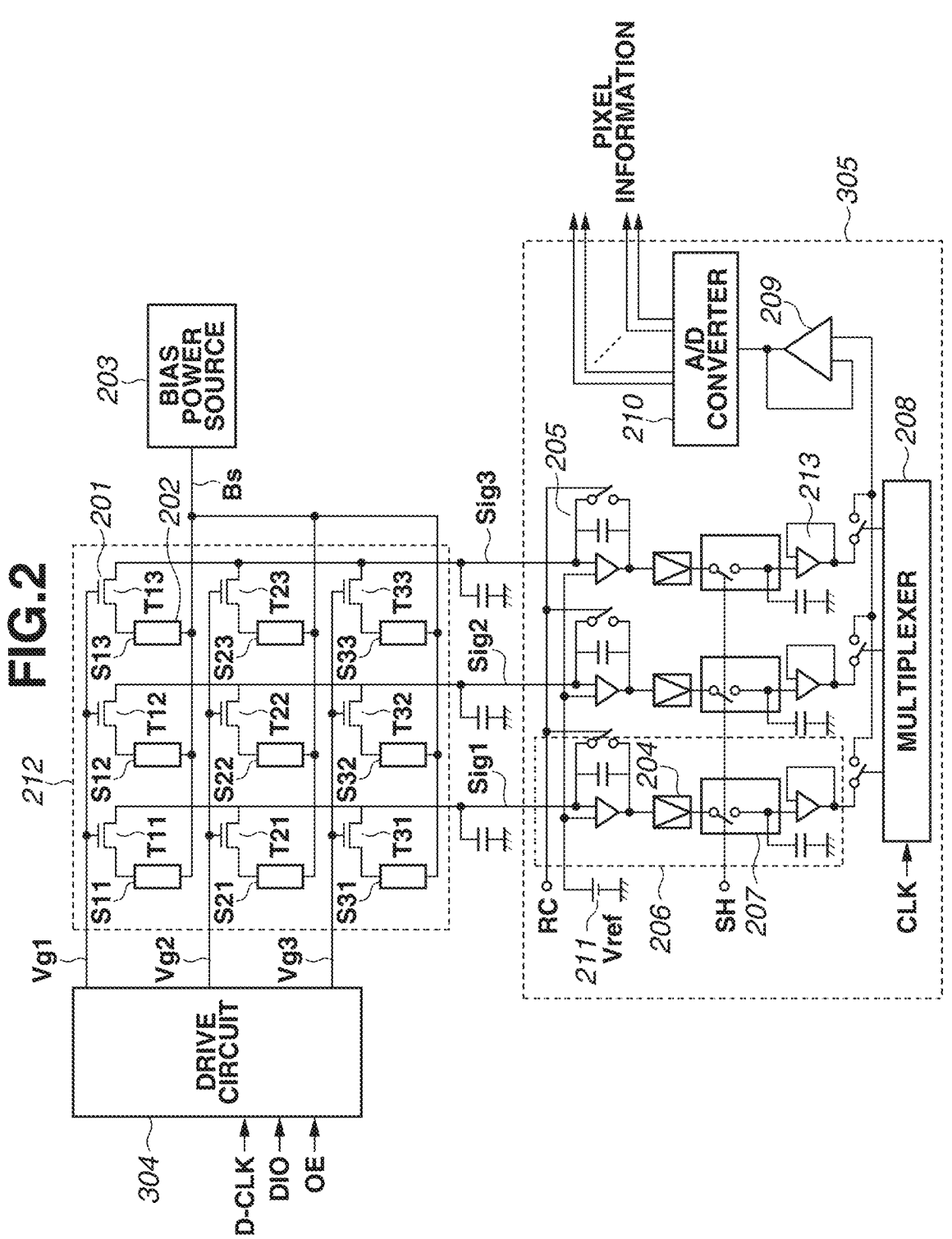
FIG. 2 is a diagram illustrating an example of a configuration of a sensor unit of a radiography apparatus according to the first exemplary embodiment.

FIG. 2 is a diagram illustrating an example of an equivalent circuit of the sensor unit of the radiography apparatus 101 according to the present exemplary embodiment. To simplify the description, FIG. 2 illustrates the radiography apparatus 101 including pixels arrayed on three rows×three columns. Nevertheless, the radiography apparatus 101 actually includes a larger number of pixels than illustrated. For example, a 17-inch radiography apparatus 101 includes pixels arrayed on about 4000 rows×about 4000 columns.

The radiography apparatus 101 includes a bias power source 203, a detection unit 212, a drive circuit 304, and a readout circuit 305.

The detection unit 212 is a two-dimensional detector including a plurality of pixels arranged in a matrix. Each pixel includes a conversion element 202 that converts radiation or light into charge, and a switch element 201 that outputs an electric signal corresponding to the charge. In the present exemplary embodiment, as a photoelectric conversion element that converts light emitted onto the conversion element 202 into charge, a positive-intrinsic-negative (PIN) photodiode that is arranged on an insulating substrate, such as a glass substrate, and contains amorphous silicon as a main material is used, but a metal insulator semiconductor (MIS) photodiode may be used instead.

As the conversion element 202, an indirect conversion element including a wavelength converter that converts radiation into light in a wavelength band that can be sensed by the photoelectric conversion element, on an irradiation side of the above-described photoelectric conversion element, or a direct conversion element that directly converts radiation into charge is desirably used.

As the switch element 201, a transistor including a control terminal and two main terminals is desirably used, and a thin-film transistor (TFT) is used in the present exemplary embodiment. One electrode of the conversion element 202 is electrically connected to one of the two main terminals of the switch element 201, and the other electrode is electrically connected with the bias power source 203 via a common bias line.

Control terminals of a plurality of switch elements 201 in a row direction, such as switch elements T11 to T13, for example, are electrically connected in common to a drive line Vg1 on the first row. A drive signal for controlling a conductive state of each of the switch elements 201 is given from the drive circuit 304 to the switch elements 201 for each row via drive lines Vg1 to Vg3.

The other main terminals of a plurality of switch elements 201 in a column direction, such as switch elements T11, T21 and T31, for example, are electrically connected to a signal line Sig1 on the first column. While the switch elements 201 are in the conductive state, electric signals corresponding to the charges of the conversion elements 202 are output to the readout circuit 305 via signal lines Sig1 to Sig3. The plurality of signal lines Sig1 to Sig3 arrayed in the column direction transmit electric signals output from a plurality of pixels, to the readout circuit 305 in parallel.

The readout circuit 305 includes amplifying circuits 206 that amplify the electric signals output in parallel from the detection unit 212, and are provided in such a manner as to correspond to the respective signal lines Sig1 to Sig3. Each of the amplifying circuits 206 includes an integrating amplifier 205 that amplifies an output electric signal, a variable amplifier 204 that amplifies an electric signal from the integrating amplifier 205, a sample-and-hold circuit 207 that samples and holds the amplified electric signal, and a buffer amplifier 213.

The integrating amplifier 205 includes an operational amplifier that amplifies the read electric signal and outputs the amplified electric signal, an integral capacitance, and a reset switch. The integrating amplifier 205 can change a gain by varying the value of the integral capacitance. The output electric signal is input to an inverting input terminal of the operational amplifier, a reference voltage Vref is input to a non-inverting input terminal of the operational amplifier from a reference power source 211, and an amplified electric signal is output from an output terminal. The integral capacitance is arranged between the inverting input terminal and the output terminal of the operational amplifier.

The sample-and-hold circuits 207 are provided in such a manner as to correspond to the respective amplifying circuits 206, and each include a sampling switch and a sampling capacitance.

The readout circuit 305 includes a multiplexer 208 that sequentially outputs electric signals read out in parallel from the amplifying circuits 206 as a serial image signal, and a buffer amplifier 209 that performs impedance conversion on the image signals to be output. An image signal that is an analog electric signal output from the buffer amplifier 209 is converted into digital image data by an analog-to-digital (A/D) converter 210, and is output to an image information processing unit 303 illustrated in FIG. 3.

The reference power source 211 supplies the reference voltage Vref to the non-inverting input terminal of the operational amplifier in each of the integrating amplifiers 205. The bias power source 203 supplies a bias voltage in common to the other electrodes of the conversion elements 202 via a bias line Bs.

Figure 3:
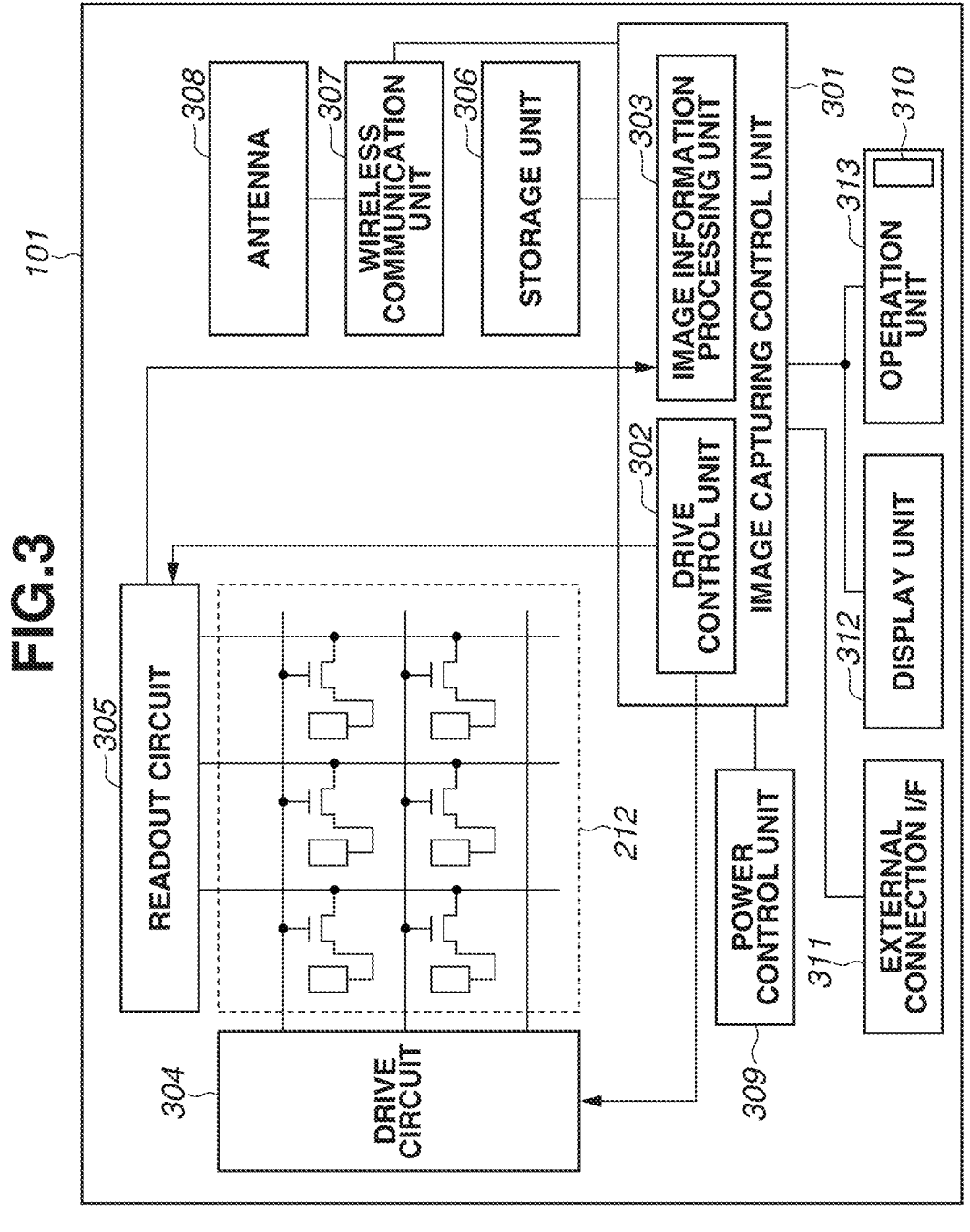
FIG. 3 is a block diagram illustrating a control signal and an image signal of the radiography apparatus.

The drive circuit 304 outputs, to the drive lines Vg1 to Vg3, a drive signal including a conducting voltage Vcom for bringing the switch elements 201 into the conductive state and a non-conducting voltage Vss for bringing the switch elements 201 into a non-conductive state, in accordance with control signals D-CLK, OE, and DIO input from a drive control unit 302 illustrated in FIG. 3. The drive circuit 304 thereby controls the conductive state and the non-conductive state of the switch elements 201, and drives the detection unit 212.

The control signal D-CLK serves as a shift clock of a shift register to be used as the drive circuit 304. The control signal DIO serves as a pulse for transfer of the shift register. The control signal OE serves as a signal for controlling an output terminal of the shift register. By performing the foregoing procedure, the drive circuit 304 sets a required drive time and a scanning direction.

The drive control unit 302 in FIG. 3 controls operations of the components of the readout circuit 305 by supplying a control signal RC, a control signal SH, and a control signal CLK to the readout circuit 305. The control signal RC is a signal for controlling the operation of the reset switch of the integrating amplifier 205. The control signal SH is a signal for controlling the operation of the sample-and-hold circuit 207. The control signal CLK is a signal for controlling the operation of the multiplexer 208.

FIG. 3 is a block diagram illustrating an example of a flow of a control signal and an image signal in the radiography apparatus 101 according to the present exemplary embodiment. The radiography apparatus 101 includes the detection unit 212, an image capturing control unit 301, the drive circuit 304, the readout circuit 305, a storage unit 306, a wireless communication unit 307, an antenna 308, a power control unit 309, an external connection interface (I/F) 311, a display unit 312, and an operation unit 313. The image capturing control unit 301 includes the drive control unit 302 and the image information processing unit 303. The operation unit 313 includes an image capturing executable state switch 310 for triggering the apparatus to transition to an image capturing executable state.

The image capturing control unit 301 controls general operations of the radiography apparatus 101, and includes the drive control unit 302 and the image information processing unit 303.

The drive control unit 302 has a function of controlling the drive circuit 304.

The image information processing unit 303 performs various types of processing on radiation image data input from the readout circuit 305. The processing to be performed by the image information processing unit 303 can include, for example, defect correction for correcting an image defect, offset correction for correcting offset data of an image, and noise reduction processing for reducing various types of noise. The image information processing unit 303 needs not execute all of processing for generating a diagnosis image, and partial processing can be performed by the console 102.

The offset correction is processing for subtracting unnecessary data, such as a dark current component, generated during the accumulation of radiation images, and is performed by subtracting offset correction image data acquired in a non-irradiated state from radiation image data acquired with radiation irradiated. Gain correction is one type of processing for correcting an image defect attributed to an individual characteristic difference among pixels arrayed in a two-dimensional matrix, and is processing for correcting a gain difference among pixels based on gain correction information data obtained by emitting radiation by a uniform dose in a state in which no subject exists.

The storage unit 306 stores radiation image data processed by the image information processing unit 303 and image capturing information in association with each other. The storage unit 306 also stores information about an imaging unit (hereinafter, imaging unit information). A nonvolatile memory, such as a flash memory, is used as the storage unit 306.

The image capturing information includes information regarding a patient of which an image has been captured, information regarding a photographer, information regarding a region of which an image has been captured, information regarding a date and time at which an image has been captured, and information such as a unique identification (ID) for identifying an image. In the case of performing image capturing in an image capturing mode in which the radiography apparatus 101 detects the start of irradiation of radiation and starts image capturing, the image capturing information also includes information used in the radiation detection determination. The imaging unit information includes information such as the name of an imaging unit, a sensor size, and a connection method (wireless, wired, etc.).

The storage unit 306 can store a single piece or a plurality of pieces of information included in the image capturing information in association with radiation image data. The storage unit 306 may further store defect information to be used for image correction and gain information for performing gain correction, and may store an operation history of the radiography apparatus 101.

The wireless communication unit 307 transmits radiation image data and image capturing information stored in the storage unit 306 to the console 102. The wireless communication unit 307 is connected to the antenna 308, and includes a circuit that transmits and receives radio waves via the antenna 308. The wireless communication unit 307 may transmit radiation image data processed by the image information processing unit 303 to a control apparatus. At this time, the wireless communication unit 307 may also store the radiation image data into the storage unit 306 at the same time with the transmission of the radiation image data. The transmission of information to the console 102 may be performed by wire communication via the external connection I/F 311.

The power control unit 309 is a unit for controlling the power of the radiography apparatus 101. A specific operation will be described below.

The display unit 312 includes a display device for displaying the state of the radiography apparatus 101. The display device displays, using a light-emitting diode (LED), the state (standby state or the image capturing executable state) of the imaging unit, and an amount of charge of a main battery 314 illustrated in FIG. 4. The display device is not limited to an LED display device, and may be a liquid crystal display or a touch-operable display.

The operation unit 313 includes a plurality of switches via which an input can be made from the outside, and includes the image capturing executable state switch 310 that triggers transition to the image capturing executable state.

Figure 4:
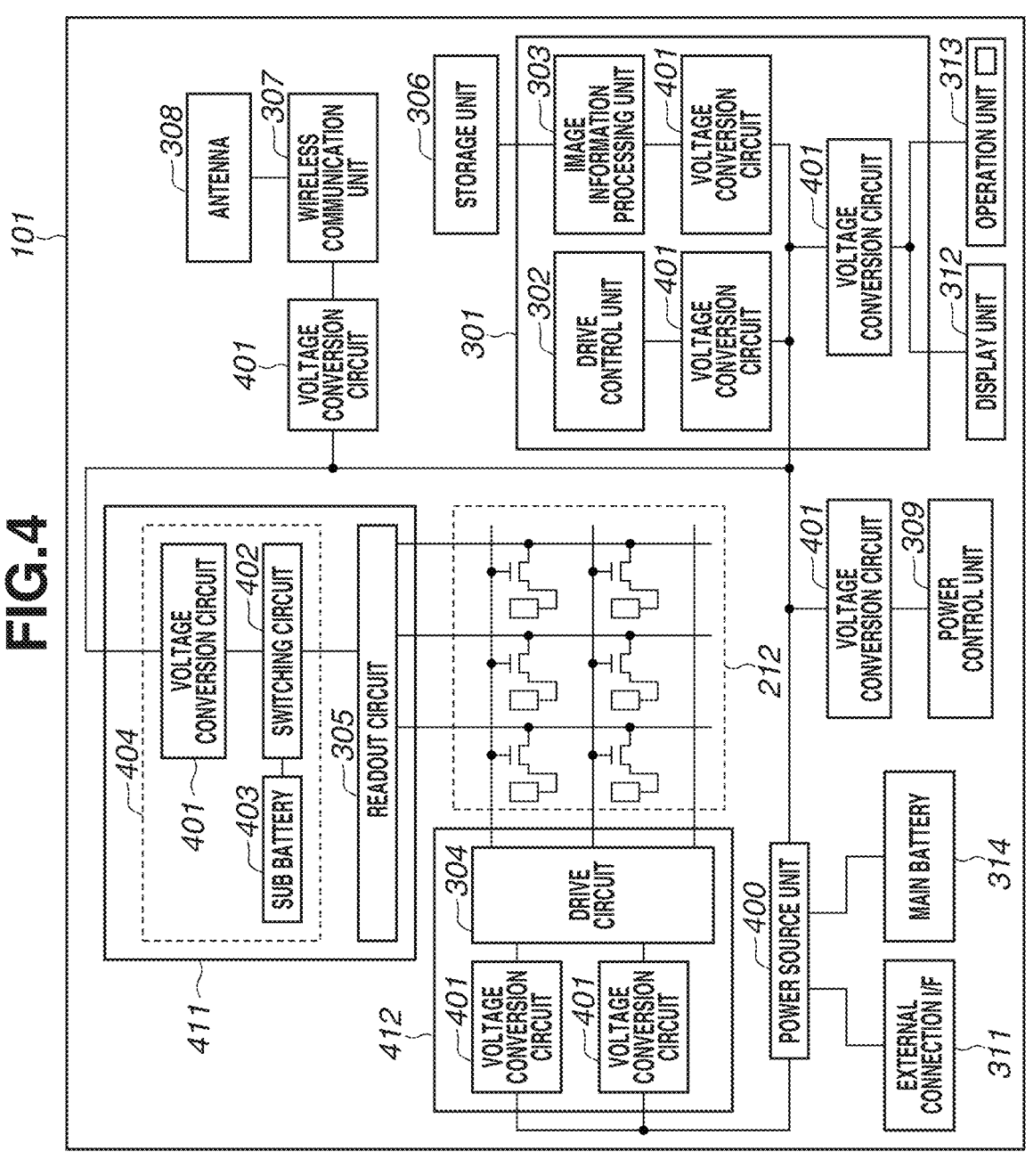
FIG. 4 is a block diagram illustrating an example of a configuration of a power supply circuit of the radiography apparatus.

FIG. 4 is a block diagram illustrating an example of power supply in the radiography apparatus 101. The radiography apparatus 101 includes the image capturing control unit 301, the main battery 314, a power source unit 400, a voltage conversion circuit 401, a readout unit 411, and a drive unit 412.

The image capturing control unit 301 includes the drive control unit 302, the image information processing unit 303, and voltage conversion circuits 401.

The readout unit 411 includes the readout circuit 305 and a small power unit 404. The small power unit 404 includes a voltage conversion circuit 401, a switching circuit 402, and a sub battery 403. The drive unit 412 includes the drive circuit 304 and voltage conversion circuits 401.

The power source unit 400 is connected to the external connection I/F 311 and is also connected to the main battery 314 attachable to and removable from the radiography apparatus 101.

A lithium ion battery is desirably used as the main battery 314, but a different type of battery may be used. For example, the main battery 314 may be a secondary battery, such as a lithium ion capacitor battery, a lithium polymer battery, a solid-state battery, or a nickel-hydrogen battery, or may be a non-rechargeable primary battery. The main battery 314 may be configured to be attachable to and detachable from the radiography apparatus 101 or may be configured to be undetachable from the radiography apparatus 101.

In the present exemplary embodiment, both of the external connection I/F 311 and the main battery 314 are connected to the power source unit 400, but either one of them may be connected to the power source unit 400.

The power source unit 400 supplies power from the power supply apparatus 104 connected to the external connection I/F 311 or from the main battery 314, to the voltage conversion circuits 401 of functional units such as the drive unit 412 and the readout unit 411.

The voltage conversion circuits 401 are each a circuit including a switching regulator, for example.

The voltage conversion circuits 401 each convert a voltage supplied from the power source unit 400 into a voltage required by each functional unit.

In the readout unit 411 in FIG. 4, the switching circuit 402 is connected to an output destination of the voltage conversion circuit 401. In addition, the sub battery 403 is connected to the switching circuit 402. Hereinafter, to simplify the description, a combination of the voltage conversion circuit 401, the switching circuit 402, and the sub battery 403 is referred to as the small power unit 404.

In FIG. 4, the small power unit 404 is provided in the readout unit 411, and the readout circuit 305 is connected to an output destination of the small power unit 404, but the small power unit 404 may be provided at another position. For example, the small power unit 404 may be provided in the drive unit 412, and the output destination of the small power unit 404 may connect to the drive circuit 304. In addition, for example, if the readout circuit 305 and the drive circuit 304 operate at the same voltage, power output from one small power unit 404 may be used by the readout circuit 305 and the drive circuit 304.

Figure 5:
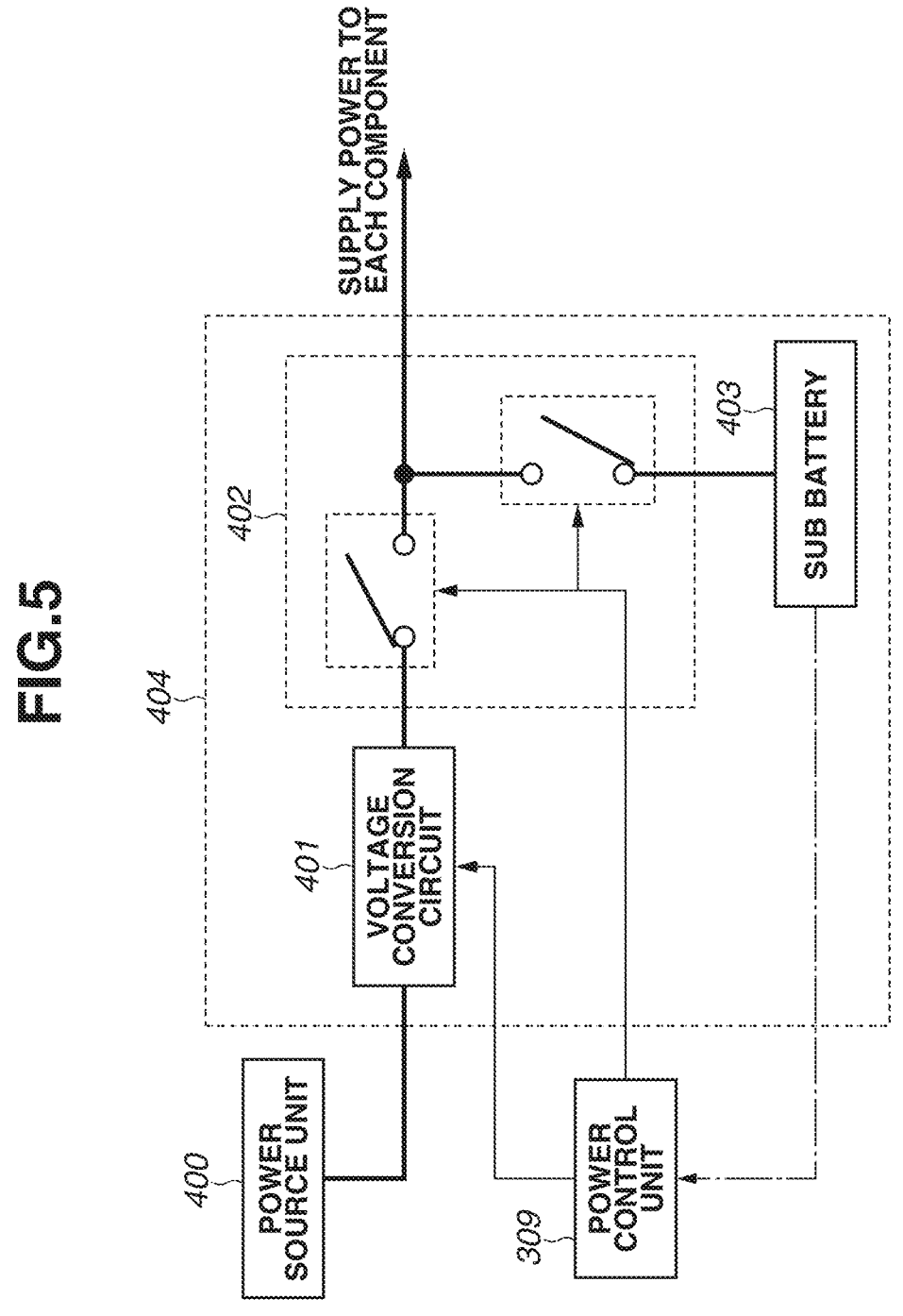
FIG. 5 is a block diagram illustrating an example of a configuration of a small power unit of the radiography apparatus.

FIG. 5 is a block diagram illustrating an example of a configuration of the small power unit 404 in FIG. 4. The small power unit 404 includes the voltage conversion circuit 401, the switching circuit 402, and the sub battery 403.

The sub battery 403 has a capacity smaller than that of the main battery 314 in FIG. 4 and is configured to be unremovable from the radiography apparatus 101. The sub battery 403 is configured to store power at a voltage converted by the voltage conversion circuit 401. That is, respective voltages of the main battery 314 and the sub battery 403 are different from each other.

The switching circuit 402 is configured to switch power supply to each connected component by switching a switch. Specifically, the switching circuit 402 can switch whether to supply power supplied from the power source unit 400 and voltage-converted by the voltage conversion circuit 401, or supply power stored in the sub battery 403.

Because the sub battery 403 stores power at the voltage converted by the voltage conversion circuit 401, it is possible to supply power to each connected component at approximately the same voltage from whichever of the voltage conversion circuit 401 and the sub battery 403.

The power control unit 309 controls the operation of the voltage conversion circuit 401 and the switching of the switch by the switching circuit 402. The power control unit 309 also monitors the voltage of the sub battery 403.

For example, if the power control unit 309 detects that the voltage of the sub battery 403 drops and a remaining amount power is low, the power control unit 309 performs control of switching the switch of the switching circuit 402 to start the charging of the sub battery 403.

The sub battery 403 is selectable from various types of batteries including a secondary battery, such as a lithium ion battery, a lithium ion capacitor battery, a lithium polymer battery, a solid-state battery, or a nickel-hydrogen battery, and a primary battery. The sub battery 403 may be configured to be attachable to and detachable from the radiography apparatus 101. The sub battery 403 can have an optimum configuration by changing the type of the sub battery 403 in accordance with voltage, current, and capacity required by each functional unit.

Figure 6:
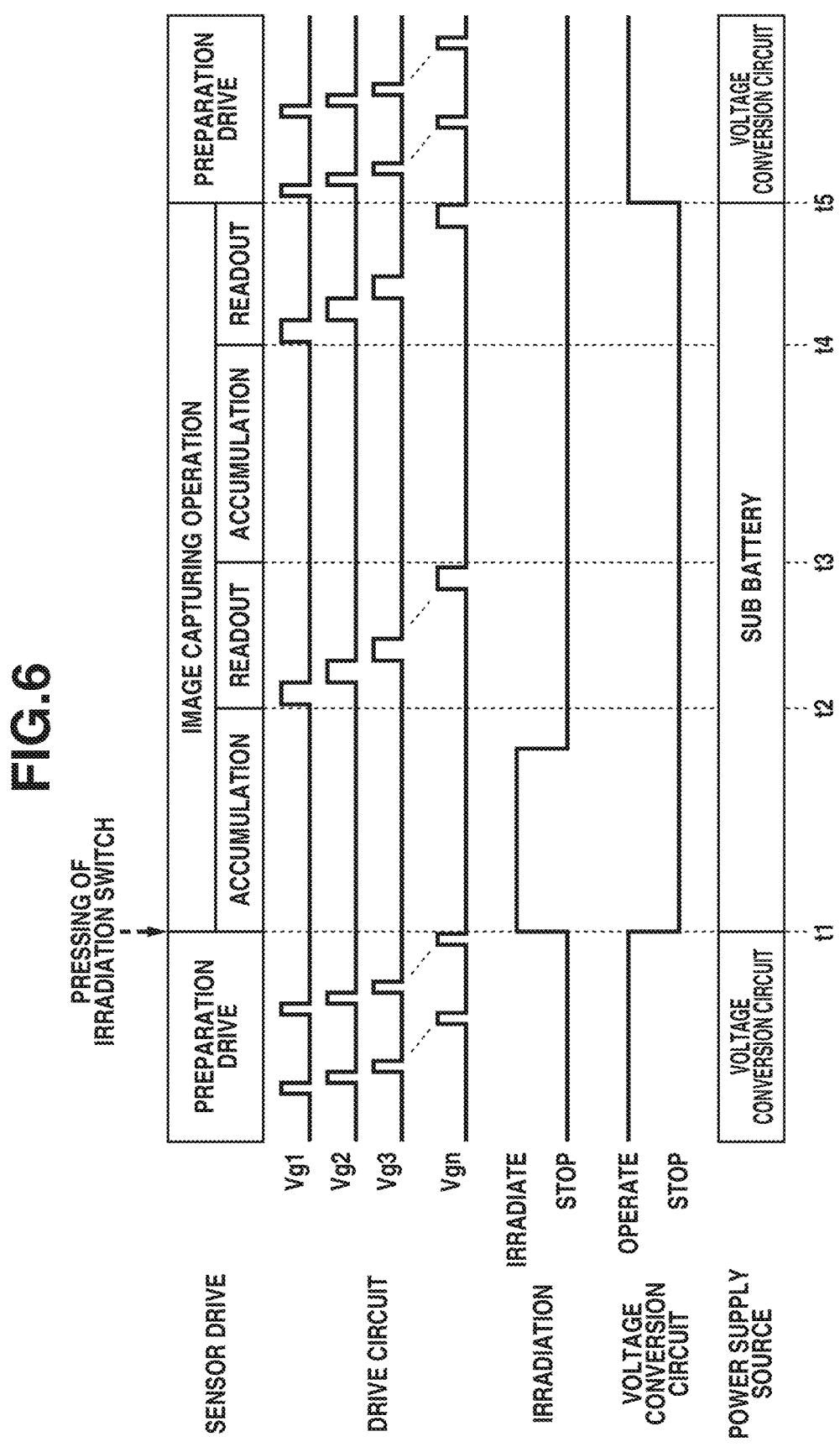
FIG. 6 is a timing chart illustrating an example of a drive sequence of the radiography apparatus.

FIG. 6 is a timing chart illustrating an example of a drive timing of the radiography apparatus 101.

If power is input to the sensor unit, the radiography apparatus 101 performs a preparation drive operation to stabilize the conversion element 202. During the preparation drive operation, a reset operation for removing charges generated by the accumulation of dark current is performed to stabilize the characteristics of the conversion element 202. The reset operation resets a dark current component of dark current flowing in the conversion element 202 by turning on or off the switch elements 201 row by row. If a predetermined amount of time elapses, the radiography apparatus 101 issues an irradiation permission notification.

At this time, the power control unit 309 operates the voltage conversion circuit 401 in the small power unit 404. The power supply to each functional unit of the radiography apparatus 101 is performed from the voltage conversion circuit 401. The sub battery 403 may be charged during the period of the preparation drive operation.

At a time t1, if the irradiation switch of the radiation generating apparatus console 107 is pressed, radiation is emitted from the radiation tube 106.

If the radiography apparatus 101 detects the irradiation of radiation based on communication with the radiation generating apparatus 108 and by various detection methods, the radiography apparatus 101 shifts from the preparation drive operation to an image capturing operation. First, the radiography apparatus 101 performs an accumulation operation. By radiation being emitted onto the radiography apparatus 101, charges are accumulated in the detection unit 212.

If the radiography apparatus 101 shifts to the image capturing operation, the power control unit 309 stops the operation of the voltage conversion circuit 401 in the small power unit 404 and switches the switch of the switching circuit 402 to perform control in such a manner as to supply power to each functional unit of the radiography apparatus 101 from the sub battery 403. During the period of the image capturing operation, the power control unit 309 continues the power supply from the sub battery 403. At this time, the operations of the voltage conversion circuits 401 other than the voltage conversion circuit 401 in the small power unit 404 need not be stopped.

At a time t2, if the radiography apparatus 101 detects the end of irradiation of radiation using various methods, such as a method of referring to a notification from the radiation generating apparatus 108 or a predetermined set time, the radiography apparatus 101 shifts to a readout operation from the accumulation operation. The readout operation reads out charges accumulated in the detection unit 212 by turning on the switch elements 201 row by row.

In times t3 to t4, to correct dark current components by the offset correction, the radiography apparatus 101 accumulates charges in the detection unit 212 over a predetermined time.

At the time t4, the radiography apparatus 101 performs an operation for reading out a signal corresponding to charges accumulated in the detection unit 212.

If the second readout operation ends, at a time t5, the radiography apparatus 101 ends the image capturing operation. After that, the radiography apparatus 101 continues to perform a preparation drive operation to be ready for the next image capturing.

If the preparation drive operation starts, the power control unit 309 may operate the voltage conversion circuit 401 in the small power unit 404 to perform control in such a manner as to supply power to each functional unit of the radiography apparatus 101 from the voltage conversion circuit 401.

By radiation being emitted in either one of the first image capturing operation and the second image capturing operation, image data for offset correction is obtained in the image capturing operation during which radiation has not been emitted.

In the present exemplary embodiment, in the first image capturing operation, a signal corresponding to charges accumulated by the irradiation of radiation is read out. Next, the radiography apparatus 101 executes the preparation drive operation for a predetermined time, performs the second image capturing operation without emitting radiation, and reads out a signal. To correct dark current components, it is desirable that an accumulation time in the second image capturing operation is as equal to an accumulation time in the first image capturing operation as possible. Also, image data for correcting dark current components may be acquired without emitting radiation in the first image capturing operation, and image data may be acquired while emitting radiation in the second image capturing operation.

As described above, in the present exemplary embodiment, during the period of the image capturing operation, the radiography apparatus 101 stops the operation of the voltage conversion circuit 401 in the small power unit 404, and supplies power from the sub battery 403. As described above, the switching regulator used in the voltage conversion circuit 401 generates high-frequency radiation noise and conductive noise. If the detection unit 212, the drive circuit 304, and the readout circuit 305 receive these types of noise at the time of the image readout operation in particular, the noise is superimposed on an image.

By stopping the operation of the voltage conversion circuit 401 in the small power unit 404 during the image capturing operation, the generation of noise is suppressed. Moreover, because the operation of the radiography apparatus 101 is continued even if the operation of the voltage conversion circuit 401 is stopped, the sub battery 403 is used, and power is supplied from the sub battery 403 during the readout operation.

An amount of noise generated from a secondary battery used as the sub battery 403 is generally smaller than an amount of noise generated from the voltage conversion circuit (switching regulator) 401. The readout circuit 305 performs the readout operation using power supplied from the sub battery 403, and accordingly it is possible to reduce noise to be superimposed on an image.

In FIG. 4, the small power unit 404 is arranged in the readout unit 411. Arranging the small power unit 404 in a portion that supplies power to a functional unit handling analog signals, such as the readout unit 411, can produce a high noise reduction effect and thus may be desirable.

In the present exemplary embodiment, the operation of the voltage conversion circuit 401 in the small power unit 404 is stopped during the period of the image capturing operation, but the period during which the operation of the voltage conversion circuit 401 is stopped may be only a period corresponding to at least one readout operation in the period of the image capturing operation.

As described above, the detection unit 212 includes a plurality of pixels. The plurality of pixels generate image signals that are based on radiation. The readout circuit 305 reads out the image signals generated by the plurality of pixels of the detection unit 212.

The voltage conversion circuit 401 converts an input voltage and outputs the converted voltage. The sub battery 403 outputs a voltage. Depending on the operating state of the radiography apparatus 101, the power control unit 309 supplies either of a voltage output by the voltage conversion circuit 401 and a voltage output by the sub battery 403 to each functional unit as a source voltage. In a case where the power control unit 309 supplies the voltage output by the sub battery 403 as a source voltage, the power control unit 309 stops the operation of the voltage conversion circuit 401.

The voltage conversion circuit 401 is a switching regulator, for example. The sub battery 403 is charged by the voltage output by the voltage conversion circuit 401.

As illustrated in FIG. 6, during the period of the preparation drive operation, the power control unit 309 supplies the voltage output by the voltage conversion circuit 401 as a source voltage, and during the period of the accumulation operation and the period of the readout operation, the power control unit 309 supplies the voltage output by the sub battery 403 as a source voltage.

The period of the preparation drive operation is a period during which a reset operation is performed to reset the plurality of pixels of the detection unit 212. The period of the accumulation operation is a period during which image signals of the plurality of pixels of the detection unit 212 are accumulated. The period of the readout operation is a period during which the readout circuit 305 reads out the image signals.

The power control unit 309 is only required to supply the voltage output by the sub battery 403 as a source voltage and stop the operation of the voltage conversion circuit 401 during at least an entire or partial period of the period during which the readout circuit 305 reads out the image signals. In other periods, the power control unit 309 operates the voltage conversion circuit 401, and supplies the voltage output by the voltage conversion circuit 401 as a source voltage.

As described above, according to the present exemplary embodiment, the radiography apparatus 101 can be used for still image capturing, such as plain radiography, or moving image capturing, such as fluoroscopy, in medical image diagnosis. The voltage conversion circuit 401 can be a noise source like a switching power source. By using the sub battery 403 in place of the voltage conversion circuit 401, the radiography apparatus 101 can acquire an image in which the influence of noise from the voltage conversion circuit 401 is reduced.

Next, a second exemplary embodiment will be described. A radiography apparatus 101 according to the second exemplary embodiment includes a plurality of small power units 404 in the radiography apparatus 101. With this configuration, it is possible to reduce noise to be superimposed on an image. The description of the second exemplary embodiment that overlaps the description of the first exemplary embodiment will be omitted.

The example of the configuration of the radiography system 100 in FIG. 1, the example of the equivalent circuit of the sensor unit in FIG. 2, the block diagram illustrating an example of a flow of the control signal and the image signal in FIG. 3, and the block diagram of the small power unit 404 in the first exemplary embodiment are also referred to in the second exemplary embodiment.

Figure 7:
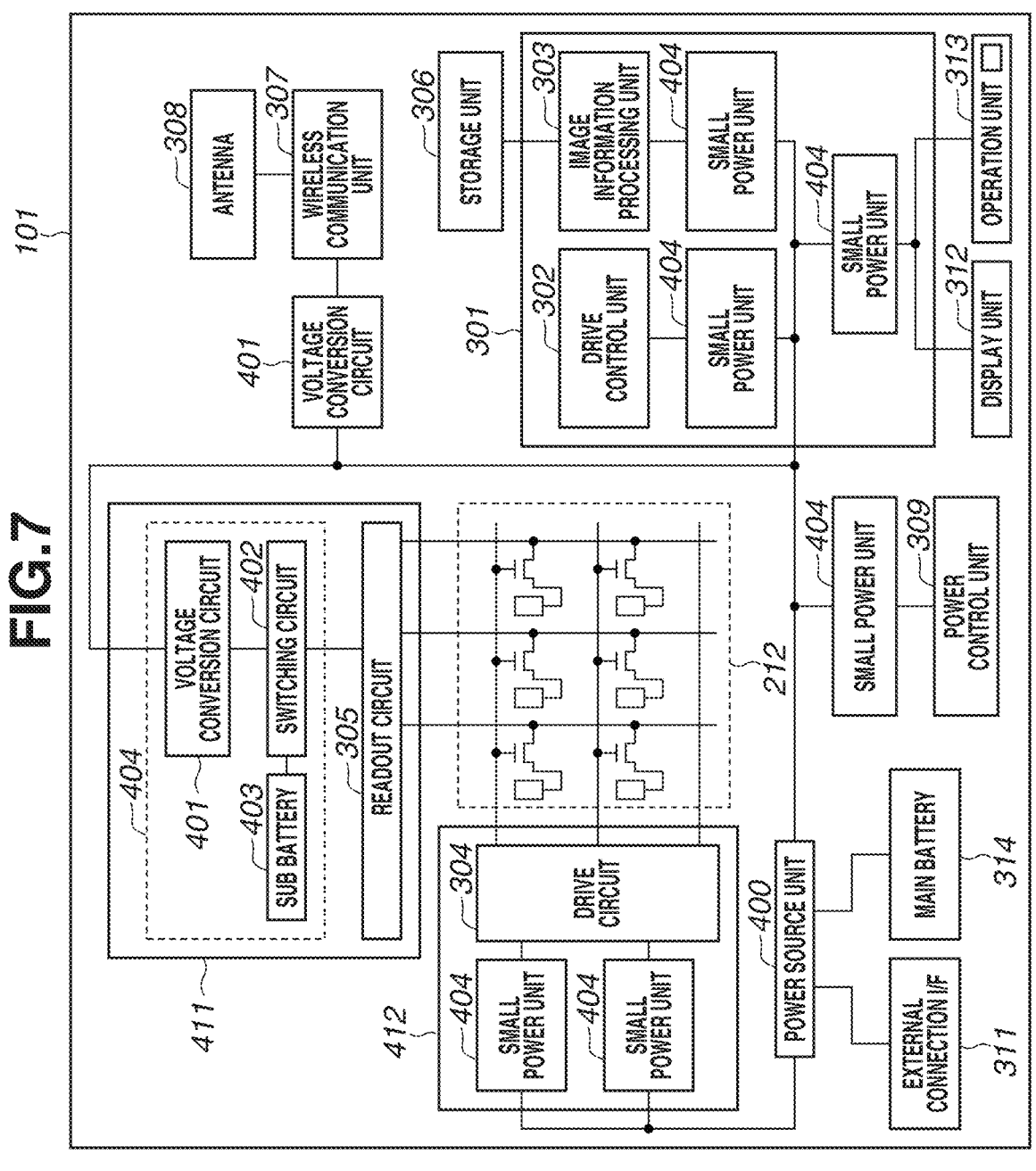
FIG. 7 is a block diagram illustrating an example of a configuration of a power supply circuit of a radiography apparatus according to a second exemplary embodiment.

FIG. 7 is a block diagram illustrating an example of power supply of the radiography apparatus 101 according to the second exemplary embodiment. The radiography apparatus 101 illustrated in FIG. 7 includes the small power units 404 in place of the voltage conversion circuits 401 of the radiography apparatus 101 illustrated in FIG. 4.

The radiography apparatus 101 includes the image capturing control unit 301, the main battery 314, the power source unit 400, the small power unit 404, the readout unit 411, and the drive unit 412.

The image capturing control unit 301 includes the drive control unit 302, the image information processing unit 303, and the small power units 404.

The readout unit 411 includes the readout circuit 305 and the small power unit 404. The small power unit 404 includes the voltage conversion circuit 401, the switching circuit 402, and the sub battery 403. The drive unit 412 includes the drive circuit 304 and the small power units 404.

The external connection I/F 311 and the main battery 314 removable from the radiography apparatus 101 are connected to the power source unit 400. The power source unit 400 supplies power from the power supply apparatus 104 connected to the external connection I/F 311 or from the main battery 314, to the small power units 404 of functional units such as the drive unit 412 and the readout unit 411.

FIG. 7 illustrates a configuration in which the small power units 404 are distributed to the functional units, but the small power units 404 may be collectively arranged, for example, near the power source unit 400.

The voltage conversion circuits 401 in the plurality of small power units 404 each convert the voltage of the power source unit 400 into a voltage required by a connection destination. The sub battery 403 is configured to store power at a voltage converted by the voltage conversion circuit 401. That is, the voltage of the sub battery 403 varies for each small power unit 404.

Not only the voltage but also a battery capacity may vary for each sub battery 403. For example, the capacity of the sub battery 403 can also be varied depending on the magnitude of power consumption at a circuit connected to the small power unit 404. Specifically, in a case where a circuit with large power consumption is connected to the small power unit 404, the capacity of the sub battery 403 is also made large. In some embodiments, setting the capacities of the plurality of sub batteries 403 in such a manner that the capacities with respect to power consumption are the same among the sub batteries 403 brings efficiency because power consumption progresses at the same rate among the plurality of sub batteries 403. In addition, the plurality of sub batteries 403 may be connected with each other in such a manner that power can be exchanged.

When the plurality of sub batteries 403 are simultaneously charged, charging current may be restricted in some cases. In these cases, the power control unit 309 can acquire information regarding remaining amounts of power in the sub batteries 403 and amounts of consumed power at the time of usage, and determine a priority order of charging the plurality of sub batteries 403 using these pieces of information. In this case, the power control unit 309 desirably controls the charging of the sub batteries 403 in such a manner that a time during which image capturing can be performed only using the sub batteries 403 is maximized.

By arranging the plurality of small power units 404 in this manner, it is possible to increase the number of voltage conversion circuits 401 of which operations can be stopped by the power control unit 309 during the period of the image capturing operation. It is therefore possible to increase a noise reduction effect. It may be desirable to arrange the small power units 404 in all the functional units in the radiography apparatus 101 as illustrated in FIG. 7. Arranging the small power units 404 in the reference power source 211 in FIG. 2 and a portion that supplies power to a functional unit, such as the drive circuit 304 and the readout circuit 305, is especially effective because not only radiation noise but also conductive noise can be reduced.

Next, an operation of the radiography apparatus 101 according to the present exemplary embodiment will be described. Regarding the operation of the voltage conversion circuit 401 connected to the power control unit 309 and the control of the switching circuit 402, in addition to performing control depending on the operating state of the radiography apparatus 101 in FIG. 6, control may be further performed depending on whether the power supply apparatus 104 and the main battery 314 are connected.

Figure 8:
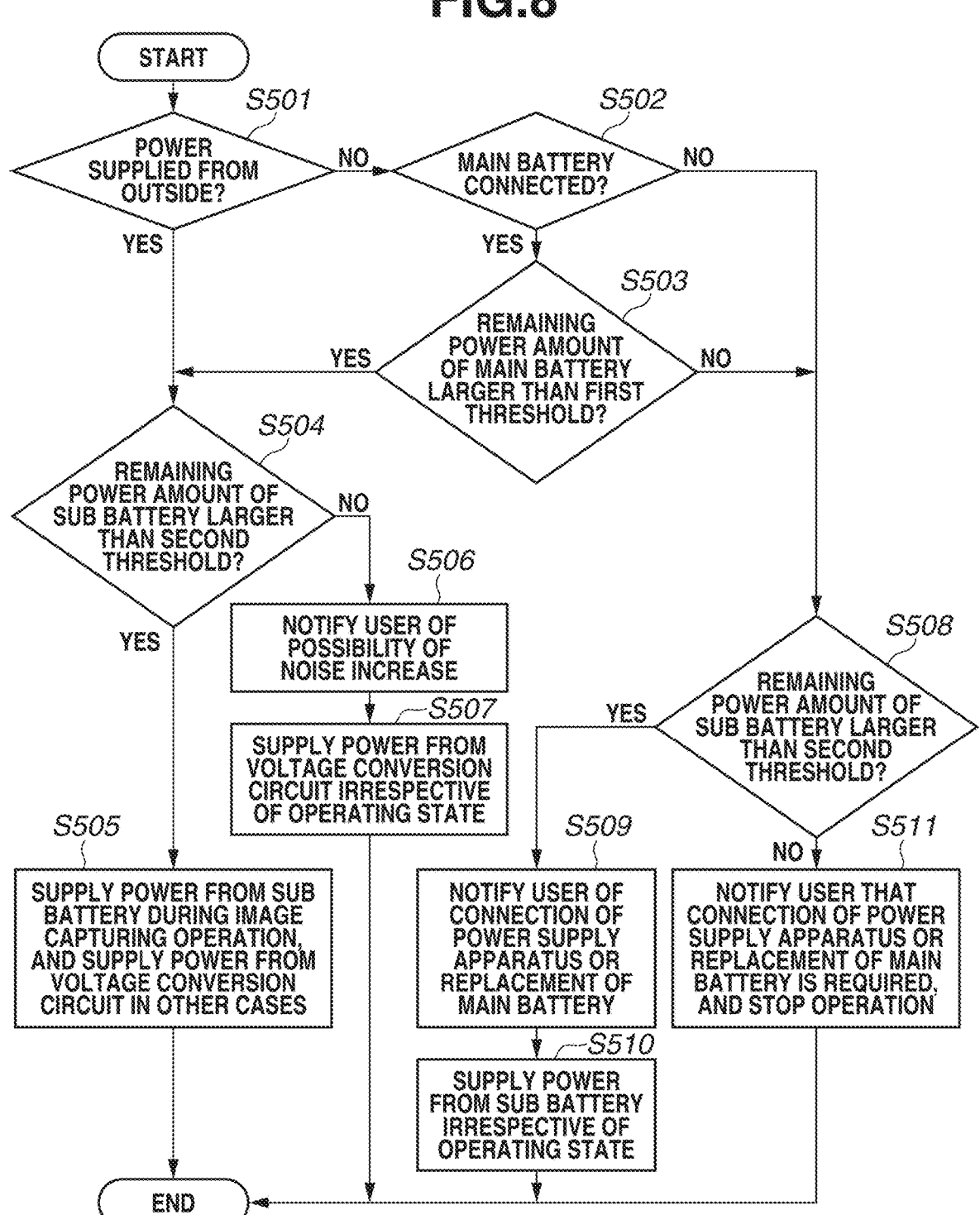
FIG. 8 is a flowchart illustrating an operation example.

FIG. 8 is a flowchart illustrating a control method of the radiography apparatus 101, and is a flowchart illustrating an example of the operation of the voltage conversion circuit 401 in the small power unit 404 and the control of the switching circuit 402.

In the present exemplary embodiment, the power control unit 309 is configured to check whether power is supplied from the outside via the external connection I/F 311, to check a connection state of the main battery 314, and to check a remaining amount of power in the main battery 314. Furthermore, the power control unit 309 is configured to check remaining amounts of power in all the sub batteries 403 in the radiography apparatus 101.

In step S501, the power control unit 309 determines whether power is supplied from the power supply apparatus 104 to the power source unit 400 via the external connection I/F 311. In a case where power is supplied from the power supply apparatus 104 to the power source unit 400 (YES in step S501), the processing proceeds to step S504. In a case where power is not supplied from the power supply apparatus 104 to the power source unit 400 (NO in step S501), the processing proceeds to step S502.

In step S502, the power control unit 309 determines whether the main battery 314 is connected to the power source unit 400. In a case where the main battery 314 is connected to the power source unit 400 (YES in step S502), the processing proceeds to step S503. In a case where the main battery 314 is not connected to the power source unit 400 (NO in step S502), the processing proceeds to step S508.

In step S503, the power control unit 309 determines whether a remaining amount of power in the main battery 314 is larger than a first threshold. In a case where a remaining amount of power in the main battery 314 is larger than the first threshold (YES in step S503), the processing proceeds to step S504. In a case where a remaining amount of power in the main battery 314 is not larger than the first threshold (NO in step S503), the processing proceeds to step S508.

In step S504, the power control unit 309 determines whether a remaining amount of power in the sub battery 403 is larger than a second threshold. In a case where a remaining amount of power in the sub battery 403 is larger than the second threshold (YES in step S504), the processing proceeds to step S505. In a case where a remaining amount of power in the sub battery 403 is not larger than the second threshold (NO in step S504), the processing proceeds to step S506.

In step S505, during the image capturing operation, the power control unit 309 stops the operation of the voltage conversion circuit 401 and supplies power from the sub battery 403 to each functional unit via the switching circuit 402. In other cases than the image capturing operation, the power control unit 309 operates the voltage conversion circuit 401 and supplies power from the voltage conversion circuit 401 to each functional unit via the switching circuit 402. A specific operation is similar to the operation described with reference to FIG. 6.

In step S506, the power control unit 309 notifies the user of a possibility that noise may increase. For example, the power control unit 309 controls the display unit 312 to display a possibility that noise may increase. After that, the processing proceeds to step S507.

In step S507, irrespective of the operating state of the radiography apparatus 101, the power control unit 309 operates the voltage conversion circuit 401 and supplies power from the voltage conversion circuit 401 to each functional unit via the switching circuit 402.

In step S508, the power control unit 309 determines whether a remaining amount of power in the sub battery 403 is larger than the second threshold. In a case where a remaining amount of power in the sub battery 403 is larger than the second threshold (YES in step S508), the processing proceeds to step S509. In a case where a remaining amount of power in the sub battery 403 is not larger than the second threshold (NO in step S508), the processing proceeds to step S511.

In step S509, because the capacity of the sub battery 403 is smaller than the capacity of the main battery 314, the power control unit 309 notifies the user of the information in such a manner as to prompt the user to connect the power supply apparatus 104 or replace the main battery 314. For example, the power control unit 309 controls the display unit 312 to provide display in such a manner as to prompt the user to connect the power supply apparatus 104 or replace the main battery 314. After that, the processing proceeds to step S510.

In step S510, irrespective of the operating state of the radiography apparatus 101, the power control unit 309 stops the operation of the voltage conversion circuit 401 and supplies power from the sub battery 403 to each functional unit via the switching circuit 402. In a case where the power supply apparatus 104 and the main battery 314 cannot be used, power is supplied from the sub battery 403. With this configuration, for example, in a case where an external power supply cable is accidentally disconnected, in a case where the remaining amount of power in the main battery 314 becomes low, or when the main battery 314 is replaced, the operation of the radiography apparatus 101 can be continued.

In step S511, the power control unit 309 notifies the user that all power sources of the radiography apparatus 101 have run out, and a connection of the power supply apparatus 104 or a replacement of the main battery 314 is required, and stops the operation of the radiography apparatus 101. For example, the power control unit 309 controls the display unit 312 to display a message indicating that a connection of the power supply apparatus 104 or a replacement of the main battery 314 is required.

As described above, depending on a state of power supply from the power supply apparatus 104, and states of the main battery 314 and the sub battery 403 in addition to the operating state of the radiography apparatus 101, the power control unit 309 performs the operation of the voltage conversion circuit 401 and the control of the switching circuit 402. With this configuration, the power control unit 309 limits power supply from the sub battery 403 to only a required case, and thus, deterioration of the sub battery 403 can be suppressed. Furthermore, the power control unit 309 utilizes the sub battery 403 in accordance with the power supply from the state of power supply from the power supply apparatus 104 and the state of the main battery 314, which makes it possible to improve the usability of the radiography apparatus 101 while reducing image noise.

Another example of the operation of the voltage conversion circuit 401 and the control of the switching circuit 402 that are performed by the power control unit 309 can be further described. For example, the power control unit 309 may perform the operation of the voltage conversion circuit 401 and the control of the switching circuit 402 depending on an amount of radiation emitted to the radiography apparatus 101.

Figure 9:
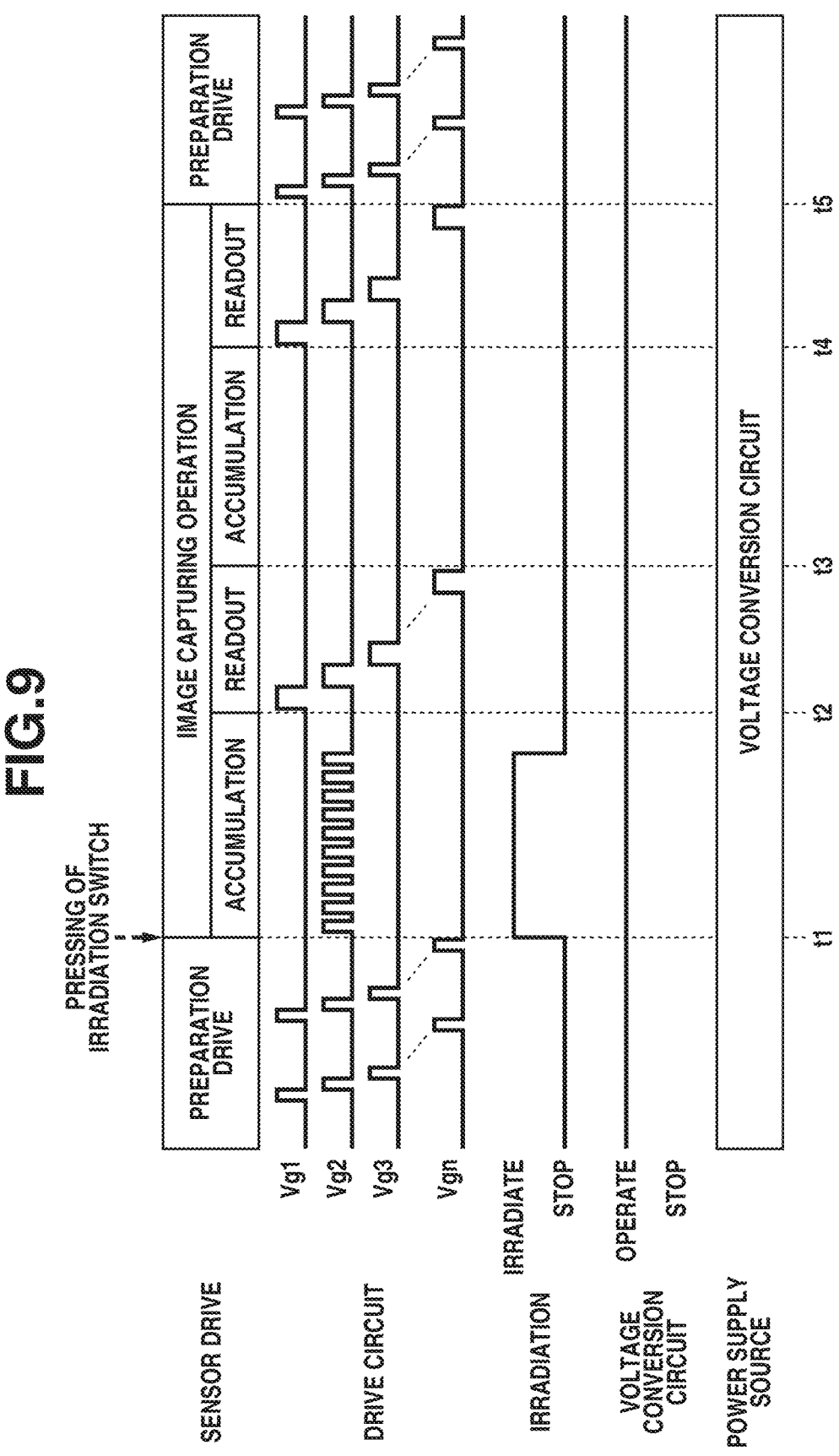
FIG. 9 is a timing chart illustrating an example of a drive sequence of the radiography apparatus.

FIG. 9 is a timing chart illustrating an example of a drive timing of the radiography apparatus 101 according to the second exemplary embodiment. FIG. 9 illustrates an operation of detecting an amount of radiation emitted to the radiography apparatus 101 in real time, by repeatedly performing readout from partial pixels of the detection unit 212 during irradiation of radiation.

At this time, the power control unit 309 is configured to receive information regarding an amount of radiation emitted to the radiography apparatus 101, from the image capturing control unit 301. The preparation drive operation to be performed before and after the image capturing operation in FIG. 9 is similar to the operation described with reference to FIG. 6.

At a time t1, if the irradiation switch of the radiation generating apparatus console 107 is pressed, radiation is emitted from the radiation tube 106. If the radiography apparatus 101 detects the irradiation of radiation, the radiography apparatus 101 shifts from the preparation drive operation to the image capturing operation. At this time, the radiography apparatus 101 enters a period of an accumulation operation, during which the readout operation is repeatedly performed on only pixels connected to the drive line Vg2, for example, while radiation is being emitted. Based on the read charges, the radiography apparatus 101 can detect an amount of radiation emitted to the radiography apparatus 101 in real time.

At a time t2, if the radiography apparatus 101 detects the end of irradiation of radiation using various methods, such as a method of referring to a notification from the radiation generating apparatus 108 or a predetermined set time, the radiography apparatus 101 shifts from the accumulation operation to the readout operation. The readout operation reads out charges accumulated in the detection unit 212 by turning on the switch elements 201 row by row.

Based on the detected radiation amount, by a time t2 when the readout operation starts, the power control unit 309 determines the operation of the voltage conversion circuit 401 and the control of the switching circuit 402 to be performed during the period from the time t2 to a time t5 when an image capturing operation ends. FIG. 9 illustrates an example in which the power control unit 309 has determined to operate the voltage conversion circuit 401 and supply power from the voltage conversion circuit 401 during the period from the time t2 to the time t5 based on the detected radiation amount.

When image capturing with a large radiation amount is performed, as compared with noise generated from the voltage conversion circuit 401 and superimposed on an image, quantum noise attributed to radiation becomes dominant as noise to be superimposed on an image. In such a case, under a use condition where the noise generated from the voltage conversion circuit 401 and superimposed on an image does not cause an issue, the power control unit 309 operates the voltage conversion circuit 401 and supplies power from the voltage conversion circuit 401 even during the image capturing operation.

In a case where a radiation amount is higher than a third threshold, irrespective of the operating state of the radiography apparatus 101, the power control unit 309 operates the voltage conversion circuit 401 and supplies power from the voltage conversion circuit 401 to each functional unit via the switching circuit 402. In a case where a radiation amount is not higher than the third threshold, the power control unit 309 performs the control illustrated in the flowchart in FIG. 8.

In this manner, in a case where noise generated from the voltage conversion circuit 401 and superimposed on an image does not cause an issue, by minimizing power supply from the sub battery 403, it is possible to reduce deterioration of the sub battery 403.

The detection method of an amount of emitted radiation is not limited to the above-described method. For example, the detection unit 212 may be provided with a dedicated pixel for radiation amount detection, or an additional sensor may be separately mounted inside or outside the radiography apparatus 101. It is also possible to receive information regarding an amount of radiation to be emitted, from console 102 or the radiation generating apparatus 108 via the wireless communication unit 307 or the external connection I/F 311.

As described above, the main battery 314 has a capacity larger than that of the sub battery 403.

In step S501, in a case where the external power supply apparatus 104 is connected (YES in step S501), the processing proceeds to step S504, and in a case where the external power supply apparatus 104 is not connected (NO in step S501), the processing proceeds to step S502.

In step S502, in a case where the main battery 314 is connected (YES in step S502), the processing proceeds to step S503, and in a case where the main battery 314 is not connected (NO in step S502), the processing proceeds to step S508.

In step S503, in a case where a remaining amount of power in the main battery 314 is larger than the first threshold (YES in step S503), the processing proceeds to step S504, and in a case where a remaining amount of power in the main battery 314 is not larger than the first threshold (NO in step S503), the processing proceeds to step S508.

In step S504, in a case where a remaining amount of power in the sub battery 403 is larger than the second threshold (YES in step S504), the processing proceeds to step S505, and in a case where a remaining amount of power in the sub battery 403 is not larger than the second threshold (NO in step S504), the processing proceeds to step S506.

In step S505, during the period of preparation drive operation, the voltage conversion circuit 401 converts a voltage that is based on the main battery 314 or the power supply apparatus 104. During the period of preparation drive operation, the power control unit 309 supplies a voltage output by the voltage conversion circuit 401 as a source voltage, and during the period of the accumulation operation and the period of the readout operation, the power control unit 309 supplies a voltage output by the sub battery 403 as a source voltage.

During at least an entire or partial period of the period during which the readout circuit 305 reads out the image signals, the power control unit 309 may supply a voltage output by the sub battery 403 as a source voltage, and stop the operation of the voltage conversion circuit 401. During other periods, the power control unit 309 operates the voltage conversion circuit 401 and supplies a voltage output by the voltage conversion circuit 401 as a source voltage.

In step S507, during the periods of preparation drive operation, the accumulation operation, and the readout operation, the voltage conversion circuit 401 converts a voltage that is based on the main battery 314 or the power supply apparatus 104. During the periods of preparation drive operation, the accumulation operation, and the readout operation, the power control unit 309 supplies a voltage output by the voltage conversion circuit 401 as a source voltage, and charges the sub battery 403.

In step S510, during the periods of preparation drive operation, the accumulation operation and the readout operation, the power control unit 309 supplies a voltage output by the sub battery 403 as a source voltage.

The radiography apparatus 101 includes a plurality of sets of voltage conversion circuits 401 and sub batteries 403. Based on the foregoing plurality of sets of voltage conversion circuits 401 and sub batteries described above, the power control unit 309 supplies a plurality of source voltages. The plurality of source voltages may be different from each other.

The power control unit 309 determines a priority order charging of the plurality of sub batteries 403 based on information regarding remaining amounts of power or amounts of consumed power of the plurality of sub batteries 403.

The power control unit 309 can supply either of a voltage output by the voltage conversion circuit 401 and a voltage output by the sub battery 403 as a source voltage, depending on a radiation amount.

In a case where the radiation amount is not larger than a third threshold, during a first period, the power control unit 309 supplies a voltage output by the sub battery 403 as a source voltage. In a case where the radiation amount is larger than the third threshold, during the first period, the power control unit 309 supplies a voltage output by the voltage conversion circuit 401 as a source voltage. The first period includes at least an entire or partial period of the period during which the readout circuit 305 reads out the image signals.

As described above, according to the present exemplary embodiment, the radiography apparatus 101 can acquire an image in which the influence of noise from the voltage conversion circuit 401 is reduced, by using the sub battery 403 in place of the voltage conversion circuit 401.

Other Exemplary Embodiments

Embodiments of the present disclosure can also be implemented by processing of supplying a program for implementing one or more functions of the above-described exemplary embodiments to a system or an apparatus via a network or a storage medium, and causing one or more processor in a computer of the system or the apparatus reading out and executing the program. Embodiments of the present disclosure can also be implemented by a circuit (for example, an application specific integrated circuit (ASIC)) for implementing the one or more functions.

The above-described exemplary embodiments each merely indicate a specific example of implementation of the present disclosure, and the technical scope of the present disclosure is not to be construed in a limited manner based on these. That is, the present disclosure can be executed in various forms without departing from its technical idea or its primary features.

According to exemplary embodiments of the present disclosure, it is possible to provide a radiography apparatus that can reduce the influence of noise from a voltage conversion circuit.

Other Embodiments

Embodiment(s) of the present disclosure can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2023-110077, which was filed on Jul. 4, 2023 and which is hereby incorporated by reference herein in its entirety.

What is claimed is:

1. A radiography apparatus comprising:
a plurality of pixels configured to generate image signals that are based on radiation;
a voltage conversion circuit configured to convert an input voltage and output the converted voltage;
a first battery configured to output a voltage; and
a power control unit configured to supply either of the voltage output by the voltage conversion circuit and the voltage output by the first battery as a source voltage, depending on an operating state of the radiography apparatus.

2. The radiography apparatus according to claim 1, wherein, in a case where the power control unit supplies the voltage output by the first battery as the source voltage, the power control unit stops an operation of the voltage conversion circuit.

3. The radiography apparatus according to claim 1, wherein the voltage conversion circuit is a switching regulator.

4. The radiography apparatus according to claim 1, wherein the first battery is charged by the voltage output by the voltage conversion circuit.

5. The radiography apparatus according to claim 1, wherein, during a first period, the power control unit supplies the voltage output by the voltage conversion circuit as the source voltage, and during a second period, the power control unit supplies the voltage output by the first battery as the source voltage.

6. The radiography apparatus according to claim 5, further comprising a readout circuit configured to read out the image signals generated by the plurality of pixels,
wherein the second period is an entire or partial period of a period during which the readout circuit reads out the image signals.

7. The radiography apparatus according to claim 6, wherein the first period is a period during which a reset operation of the plurality of pixels is performed.

8. The radiography apparatus according to claim 5, wherein the first period is a period during which a reset operation of the plurality of pixels is performed.

9. The radiography apparatus according to claim 5, further comprising a readout circuit configured to read out the image signals generated by the plurality of pixels,
wherein the first period is a period during which a reset operation of the plurality of pixels is performed, and
wherein the second period is a period during which the readout circuit reads out the image signals.

10. The radiography apparatus according to claim 5, further comprising a readout circuit configured to read out the image signals generated by the plurality of pixels,
wherein the first period is a period during which a reset operation of the plurality of pixels is performed, and
wherein the second period includes a period during which the image signals of the plurality of pixels are accumulated and a period during which the readout circuit reads out the image signals.

11. The radiography apparatus according to claim 1,
wherein, in a case where a second battery having a capacity larger than that of the first battery or an external power supply apparatus is connected, during a period during which a reset operation of the plurality of pixels is performed, the voltage conversion circuit converts a voltage that is based on the second battery or the external power supply apparatus, and the power control unit supplies the voltage output by the voltage conversion circuit as the source voltage, and
wherein, in a case where the second battery having a capacity larger than that of the first battery is not connected, and in a case where an external power supply apparatus is not connected, during the period during which the reset operation of the plurality of pixels is performed, the power control unit supplies the voltage output by the first battery as the source voltage.

12. The radiography apparatus according to claim 1, wherein, in a case where a second battery having a capacity larger than that of the first battery is connected and a remaining amount of power in the second battery is larger than a first threshold, during a period during which a reset operation of the plurality of pixels is performed, the voltage conversion circuit converts a voltage that is based on the second battery, and the power control unit supplies the voltage output by the voltage conversion circuit as the source voltage, and wherein, in a case where the second battery having a capacity larger than that of the first battery is connected and the remaining amount of power in the second battery is not larger than the first threshold, during the period during which the reset operation of the plurality of pixels is performed, the power control unit supplies the voltage output by the first battery as the source voltage.

13. The radiography apparatus according to claim 1, further comprising a readout circuit configured to read out the image signals generated by the plurality of pixels, wherein, in a case where a remaining amount of power in the first battery is larger than a second threshold, during an entire or partial period of a period during which the readout circuit reads out the image signals, the power control unit supplies the voltage output by the first battery as the source voltage, and wherein, in a case where the remaining amount of power in the first battery is not larger than the second threshold, during the period during which the readout circuit reads out the image signals, the power control unit supplies the voltage output by the voltage conversion circuit as the source voltage.

14. The radiography apparatus according to claim 13, wherein, in a case where the remaining amount of power in the first battery is not larger than the second threshold, during the period during which the readout circuit reads out the image signals, the power control unit supplies the voltage output by the voltage conversion circuit as the source voltage, and charges the first battery.

15. The radiography apparatus according to claim 1, further comprising a plurality of sets of voltage conversion circuits and first batteries, wherein the power control unit supplies a plurality of source voltages based on the plurality of sets of voltage conversion circuits and first batteries.

16. The radiography apparatus according to claim 15, wherein the plurality of source voltages are different from each other.

17. The radiography apparatus according to claim 15, wherein the power control unit determines a priority order of charging the plurality of first batteries based on information regarding remaining amounts of power or amounts of consumed power of the plurality of first batteries.

18. The radiography system comprising:
the radiography apparatus according to claim 1; and
a radiation source configured to emit radiation.

19. A radiography apparatus comprising:
a plurality of pixels configured to generate image signals based on radiation;
a voltage conversion circuit configured to convert an input voltage and output the converted voltage;
a first battery configured to output a voltage; and
a power control unit configured to supply either of the voltage output by the voltage conversion circuit and the voltage output by the first battery as a source voltage, depending on a radiation amount.

20. A control method for a radiography apparatus, the radiography apparatus including:
a plurality of pixels configured to generate image signals based on radiation;
a voltage conversion circuit configured to convert an input voltage and output the converted voltage; and
a first battery configured to output a voltage,
the method comprising:
supplying either of the voltage output by the voltage conversion circuit and the voltage output by the first battery as a source voltage, depending on an operating state of the radiography apparatus.

* * * * *